(12) United States Patent
Cobianu et al.

(10) Patent No.: US 9,604,191 B2
(45) Date of Patent: Mar. 28, 2017

(54) METHOD AND SYSTEM FOR FLAMMABLE GAS DETECTION COMPRISING A SONICATED NANOSTRUCTURED METAL OXIDE

(71) Applicant: HONEYWELL INTERNATIONAL INC., Morristown, NJ (US)

(72) Inventors: Cornel P. Cobianu, Bucharest (RO); Bogdan-Catalin Serban, Bucharest (RO); Alisa Stratulat, Bucharest (RO); Viorel Georgel Dumitru, Prahova (RO); Mihai Brezeanu, Bucharest (RO); Octavian Buiu, Bucharest (RO)

(73) Assignee: Honeywell International Inc., Morris Plains, NJ (US)

( * ) Notice: Subject to any disclaimer, the term of this patent is extended or adjusted under 35 U.S.C. 154(b) by 46 days.

(21) Appl. No.: 14/813,620

(22) Filed: Jul. 30, 2015

(65) Prior Publication Data

US 2016/0038908 A1 Feb. 11, 2016

(30) Foreign Application Priority Data

Aug. 7, 2014 (EP) .................................... 14180280

(51) Int. Cl.
| | | |
|---|---|---|
| *G01N 33/00* | (2006.01) | |
| *G01N 27/26* | (2006.01) | |
| *G01N 27/04* | (2006.01) | |
| *B01J 19/10* | (2006.01) | |
| *C01G 19/02* | (2006.01) | |
| *G01N 27/12* | (2006.01) | |

(52) U.S. Cl.
CPC .............. *B01J 19/10* (2013.01); *C01G 19/02* (2013.01); *G01N 27/04* (2013.01); *G01N 27/127* (2013.01); *G01N 27/26* (2013.01); *G01N 33/0036* (2013.01); *C01P 2002/54* (2013.01); *C01P 2004/64* (2013.01)

(58) Field of Classification Search
CPC ..... B01J 19/10; G01N 27/127; G01N 27/125; G01N 33/0036–33/0057
See application file for complete search history.

(56) References Cited

U.S. PATENT DOCUMENTS

2013/0004412 A1 1/2013 Iyer et al.

OTHER PUBLICATIONS

"European Application Serial No. 14180280.1, Extended European Search Report mailed Feb. 27, 2015", 6 pgs.
"European Application Serial No. 14180280.1, Response filed Jun. 29, 2015 to Extended European Search Report mailed Feb. 27, 2015", 13 pgs.
Bagal, L K, et al., "Influence of Pd-ioading on gas sensing characteristics of $SnO_2$ thick films", *Ceramics International*, 38(6), (2012), 4835-4844.
Chakraborty, S, et al., "Complex plane impedance plot as a figure of merit for tin dioxide-based methane sensor", *Sensors and Actuators B: Chemical*, 119(2), (2006), 431-434.
Choi, J. K., et al., "Design of selective gas sensors using electrospun Pd-doped $SnO_2$ hollow nanofibers", *Sensors and Actuators B: Chemical*, 150(1), (2010), 191-199.

*Primary Examiner* — Christopher A Hixson
(74) *Attorney, Agent, or Firm* — Schwegman Lundberg & Woessner, P.A.

(57) ABSTRACT

The present disclosure relates to a nanostructured palladium-based flammable gas detector synthesized using sonochemistry. The nanostructured palladium-based flammable gas detectors may use nanostructured sensing materials to allow reduction of power consumption, where the nanostructures reduce power consumption due to their large specific area and increased porosity. The nanostructures may increase the number of active sensing sites, allowing the surface energy to be high enough for sensing reactions to occur without requiring significant external thermal energy.

20 Claims, 5 Drawing Sheets

METHOD AND SYSTEM FOR FLAMMABLE GAS DETECTION COMPRISING A SONICATED NANOSTRUCTURED METAL OXIDE

CROSS REFERENCE TO RELATED APPLICATIONS

The present application claims priority to European Patent Application No. EP 14180280.1, entitled Method and System for Flammable Gas Detection, filed on Aug. 7, 2014, the content of which is hereby incorporated herein in its entirety.

BACKGROUND

The ability to detect toxic and flammable gasses is important for the safe operation of numerous, highly complex industrial enterprises. Both fixed and portable detectors are currently used to detect toxic and flammable gases released from industrial processes. In order to reduce detection interruptions, low-power gas sensors have been used to increase portable detector battery life, Various systems are known for the detection of flammable gasses. Some of the flammable gas detection systems include Micro-Electro-Mechanical Systems (MEMS) technologies, however the reliability and long-term stability of these MEMS gas detectors has not yet reached the commercial stage. Various flammable gas detection systems have included commercial platinum wire resistance-based pellistor flammable gas sensors, however portable detector battery life can be shortened by the power consumption in such sensors. Such a commercial pellistor consists of a platinum-coiled wire covered by bead-like catalyst, which is generally made of metal oxides on which noble metals are deposited. In other cases, a noble metal is incorporated in the body of the bead. The platinum wire may function as a heater for the bead, as well as a temperature sensor.

Detection of flammable gases (e.g., methane ($CH_4$), propane ($C_3H_8$), butane ($C_4H_{10}$), hydrogen ($H_2$), and carbon monoxide (CO)) is of high importance for safety and process control in coal and petrochemical industries, as well as for safety of homes and buildings, where flammable gases are burned for heating and cooking Some flammable gas sensors include a thick film of $SnO_2$ deposited on ceramic substrate, where the ceramic substrate is heated by a platinum heater. Such a ceramic sensor is seldom employed in portable applications, as it may consume about 850 mW for heating the substrate to the optimum sensing temperature and reading the detector response. A high level of power consumption in any portable application requires frequent battery replacement, which may raise both productivity and safety issues in field operation, These sensors also include limited flammable gas sensitivity, sometimes detecting flammable gases only at relatively high concentrations, including above 500 ppm. In safety applications, it may be useful to detect lower gas concentrations and provide an early alarm against a potentially or currently hazardous situation.

SUMMARY

Flammable gas sensors may be improved by decreasing power consumption and increasing sensitivity, ideally to power levels below 100 mW and sensitivity to concentrations below 100 ppm. Preferably, a new flammable gas sensor should exhibit lower power consumption than existing flammable gas sensors, and exhibit sufficiently high surface energy for sensing reactions without requiring significant external thermal energy.

A nanostructured palladium-based flammable gas detector with reduced power consumption may be synthesized using sonochemistry. The nanostructured sensing materials may reduce power consumption due to the large specific area and increased porosity of the nanostructured materials. The nanostructures may increase the number of active sensing sites, allowing the surface energy to be high enough for sensing reactions to occur without requiring significant external thermal energy.

DETAILED DESCRIPTION OF THE DRAWINGS

The embodiments of the present invention will be described, by way of example only, by reference to the accompanying drawings.

DETAILED DESCRIPTION

Figure 1:
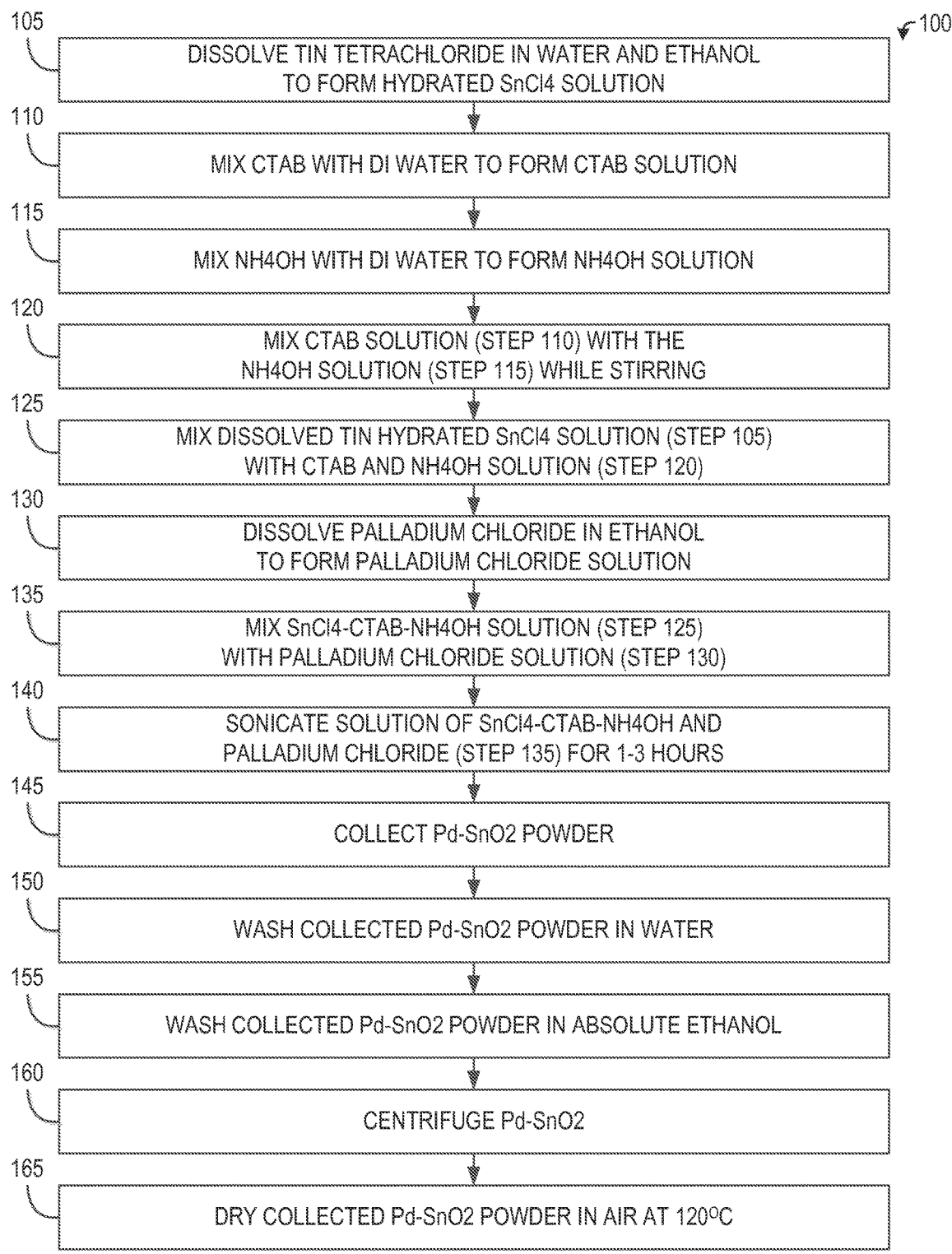
FIG. 1 is a first example method of sonochemical synthesis of nanostructured palladium-doped $SnO_2$ nanocomposite and sensor fabrication.

A flammable gas sensor may be formed from a metal oxide, where the sensing layer may consist of palladium-doped tin dioxide prepared using a sonochemistry method. The addition of nanostructuring guiding agents (e.g., DMF, P123, CTAB) to the sonochemical synthesis may enable control of grain size and powder architecture. The resulting nanostructured sensing layer generated by using sonochemistry may allow the surface energy to be high enough for sensing reactions to occur without requiring significant external thermal energy.

Sonochemistry is a synthesis method, where the chemical reactions are developed in the presence of high intensity ultrasound waves, which are irradiating the solution. Because of these ultrasound waves propagating in the liquid, a periodic increase and decrease of the pressure in the liquid occurs, and thus gas bubbles appear in the liquid. The gas pressure inside the bubbles can be as high as 1000 bar. These bubbles are initially growing by the energy received from the ultrasound waves, but at a certain moment, they can no longer receive this energy, and then, bubbles implosion occurs. This is so-called cavitation process. Due to the gas bubbles implosion, the local chemical reactions, mass transport, and the hierarchical structuring processes (e.g., nanostructuring processes) are all enhanced by the local high temperatures (5000 K), local heating and cooling rates ($10^9$ K/s), pressures (1000 bar) and fluid mass velocities (1000 Km/h), which are developed at the frontier between the liquid and the imploding gas bubbles. Sonochemical sol-gel synthesis may consist of a sequence of cavitation-enhanced chemical reactions specific to sol-gel (e.g., dissolution, hydrolysis, or polycondensation), to which specific effects of guided hierarchical nanostructuring are added. Various apparatuses for sonochemical synthesis may be used, such as the UIS250V apparatus provided by Hielscher Ultrasonic GmbH.

The sonochemistry method also enables increased control over layer structuring (e.g., layer nanostructuring), such as by adjusting the value of power or intensity of acoustic radiation applied during cavitation-activated chemical reactions between desired precursors and reagents. Specific reagents (e.g., triblock copolymer, poly (ethylene glycol)-poly (propylene glycol)-poly (ethylene glycol) triblock copolymer, or P123) may be selected for guiding the nanostructuring, such as during the formation of nanowires, nanoflowers, nanofibers, or other nanostructures. 100171 Sonochemical synthesis of Pd—$SnO_2$ may result in a Pd—$SnO_2$ solution, which may be reduced to a powder of nanostructured metal oxide by washing, filtrating, and drying of the solution. The nanostructured powder may then be mixed with a binder to obtain a slurry of controlled viscosity. The slurry may be deposited as a thick or thin sensing film on an interdigitated metal electrode structure deposited on a substrate. After thermal consolidation of the sensing layer, the resulting chemo-resistor may be used for flammable gas detection.

Palladium doping may be used to enhance the flammable gas detection by electronic and chemical sensitization mechanisms specific to palladium. Electronic sensitization may result from the ambient oxidation of Pd. For example, Pd may oxidize to PdO at standard temperature and pressure (STP) and be reduced back to Pd in the presence of flammable reducing gases (e.g., $CH_4$, CO, $H_2$), where the reduction of PdO to Pd may give electrons back to the sensing material and thereby decrease the electrical resistance. Chemical sensitization may result from palladium catalyzing the dissociation of the oxygen molecules to ionized oxygen atoms. The ionized oxygen atoms may move from the palladium surface to the tin oxide surface, increasing the depletion region of the semiconductor, which may increase the concentration of surface oxygen ions and increase sensor resistance in clean air. In the presence of flammable reducing gases, oxygen ions may react with the reducing gases and give electrons back to the tin oxide, thereby decreasing the electrical resistance.

FIG. 1 is a first example method of sonochemical synthesis of nanostructured palladium-doped $SnO_2$ nanocomposite and sensor fabrication 100. In this first method 100, the precursors may include tin tetrachloride and palladium chloride. Chemical reagents for precursor dissolution and controlling hydrolysis, polycondensation, and nanostructuring may include deionized water DI), monoterpene alcohol (e.g., ethanol), ammonium hydroxide, and a cationic surfactant. The cationic surfactant may be cetyltrirnethylamrnonium bromide (CTAB) or another tetraalkylammonium salt. The tetraalkylammonium salt may be described by the general formula $R_1R_2R_3R_4N^+X^-$. For example, $R_1$ may be $C_{12}$-$C_{24}$ n-alkyl; $R_2$, $R_3$, and $R_4$ may be methyl, ethyl, propyl, butyl, pentyl, hexyl, benzyl, or combinations of these radicals; and X may be $Br^-$, $Cl^-$, or $I^-$. The surfactants may be aimed at guiding and enhancing nanostructuring of the powder during consolidation process. The target of the synthesis may be preparation of 0.1-2.0 percentage by weight of PCl—$SnO_2$ powder, At 105, an appropriate amount of tin tetrachloride ($SnCl_4$) may be dissolved in water and ethanol to form a hydrated $SnCl_4$ solution. At 110, CTAB (or another tetraalkylammonium salt) may be mixed with DI water to form a CTAB solution. At 115, $NH_4OH$ may be mixed with DI water to form an $NH_4OH$ solution. At 120, the CTAB solution may be mixed with the $NH_4OH$ solution while stirring. At 125, the hydrated $SnCl_4$ solution may be mixed with the CTAB—$NH_4OH$ solution. At 130, an appropriate amount of palladium chloride may be dissolved in in ethanol to form a palladium chloride solution. At 135, the palladium chloride solution may be mixed with the $SnCl_4$—CTAB—$NH_4OH$ solution from 125. At 140, the solution of palladium chloride an $SnCl_4$—CTAB—$NH_4OH$ may be sonicated for 1-3 hours to form a Pd—$SnO_2$ solution. For example, the sonication may be performed by exposing the solution of palladium chloride and $SnCl_4$—CTAB-$NR_4OH$ to 24 KHz acoustic irradiation at 100 W for the 1-3 hour duration, such as using a Hieischer Ultrasonics sonicator. The Pd—$SnO_2$ powder may be collected from the Pd—$SnO_2$ solution at 145, washed with DI water at 150, washed with absolute ethanol at 155, centrifuged at 160 and finally dried in air at 120° C. at 165. Following 165, the Pd—$SnO_2$ powder may be used to prepare thin sensing film or thick sensing film, as shown and described with respect to FIGS. 5A-5B.

Figure 2:
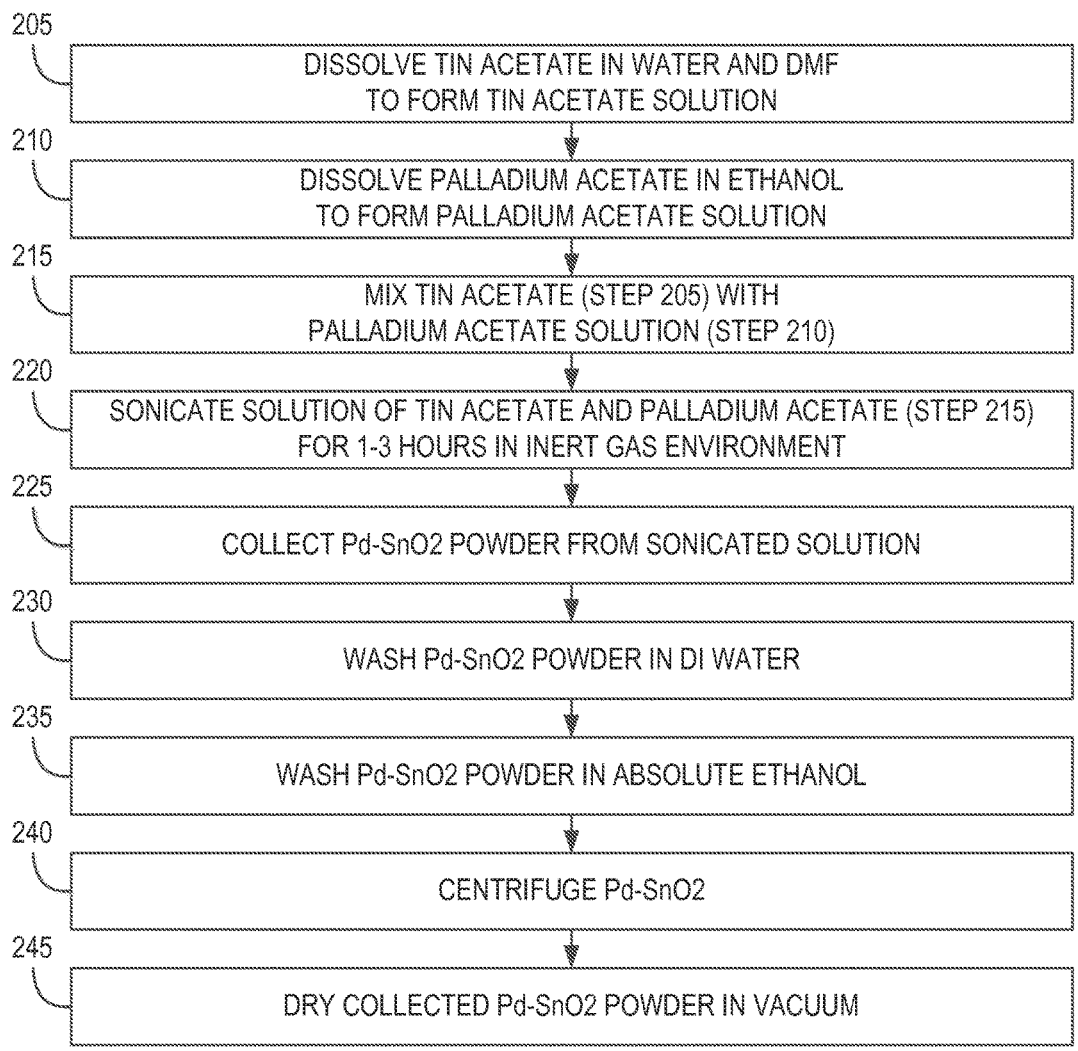
FIG. 2 is a second example method of sonochemical synthesis of nanostructured palladium-doped $SnO_2$ nanocomposite and sensor fubrication.

FIG. 2 is a second example method of sonochemical synthesis of nanostructured palladium-doped $SnO_2$ nanocomposite and sensor fabrication 200. In this second method 200, the precursors may include tin acetate and palladium acetate. Chemical reagents for precursor dissolution and controlling hydrolysis, polycondensation, and nanostructuring may include ethanol ($C_2H_5OH$), DI water, and a nanostructuring surfactant such as dimethylformamide ("DMF," or $C_3H_7NO$). The target of the synthesis is preparation of Pd—$SnO_2$.

At 205, an appropriate amount of tin acetate may be dissolved in DMF and deionized (DI) water to form an aqueous solution of tin acetate. At 210, an appropriate amount of palladium acetate may be dissolved in ethanol to form a palladium acetate solution. At 215, the tin acetate solution may be mixed with the palladium acetate solution. At 220, the solution of tin and palladium acetate may be sonicated for 1-3 hours to form a Pd—$SnO_2$ solution. For example, the sonication may be performed by exposing the solution to 24 KHz acoustic irradiation at 100 W for the 1-3 hour duration. The Pd—$SnO_2$ powder may be collected from the Pd—$SnO_2$ solution at 225, washed with DI water at 230, washed with absolute ethanol at 235, centrifuged at 240, and dried in a vacuum at 245. Following 245, the Pd—$SnO_2$ powder may be used to prepare thin sensing film or thick sensing film, as shown and described with respect to FIGS. 5A-5B.

Figure 3:
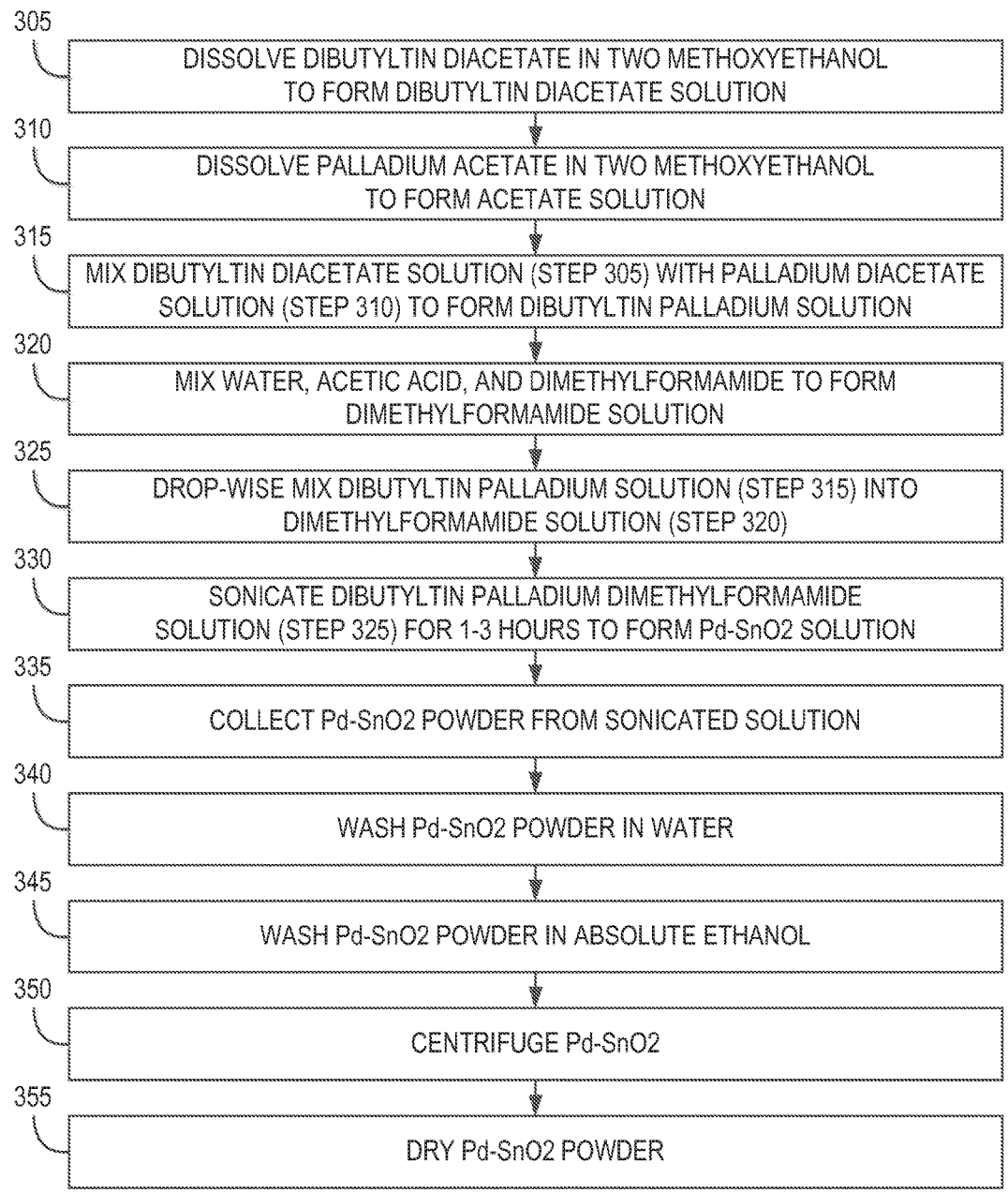
FIG. 3 is a third example method of sonochemical synthesis of nanostructured palladium-doped $SnO_2$ nanocomposite and sensor fabrication.

FIG. 3 is a third example method of sonochernical synthesis of nanostructured paliadium-doped $SnO_2$ nanocomposite and sensor fabrication 300. In this third method 300, the precursors may include dibutyltindiacetate ($C_{12}H_{24}O_4Sn$) and palladium acetate ($Pd(CH_3COO)_2$). Chemical reagents for precursor dissolution and controlling hydrolysis, polycondensation, and nanostructuring may include 2-methoxyethanol, DI water, and dimethylformamide (DMF).

At 305, an appropriate amount of dibutyltin diacetate may be dissolved in dehydrated 2-methoxyethanol to form a dibutyltin diacetate solution. At 310, an appropriate amount of palladium acetate is dissolved in dehydrated 2-methoxyethanol to form a palladium acetate solution. At 315, the dibutyltin diacetate solution is mixed with the palladium acetate solution to form a dibutyltin palladium acetate solution. At 320, an appropriate amount of water, acetic acid, and dimethylformamide are mixed to form a dimethylformamide solution. At 325, the dibutyltin palladium acetate solution from 315 may be drop-wise mixed into the dimethylformamide solution from 320. At 330, the dibutyltin palladium dimethylformamide solution may be sonicated for 1-3 hours to form a Pd—SnO$_2$ solution. For example, the sonication may be performed by exposing the solution to 24 KHz acoustic irradiation at 100 W for the 1-3 hour duration. The Pd—SnO$_2$ powder may be collected from the Pd—SnO$_2$ solution at 335, washed with water at 340, washed with absolute ethanol at 345, centrifuged at 350 and dried at 355. Following 355, the Pd—SnO$_2$ powder may be used to prepare thin sensing film or thick sensing film, as shown and described with respect to FIGS. 5A-5B.

Figure 4:
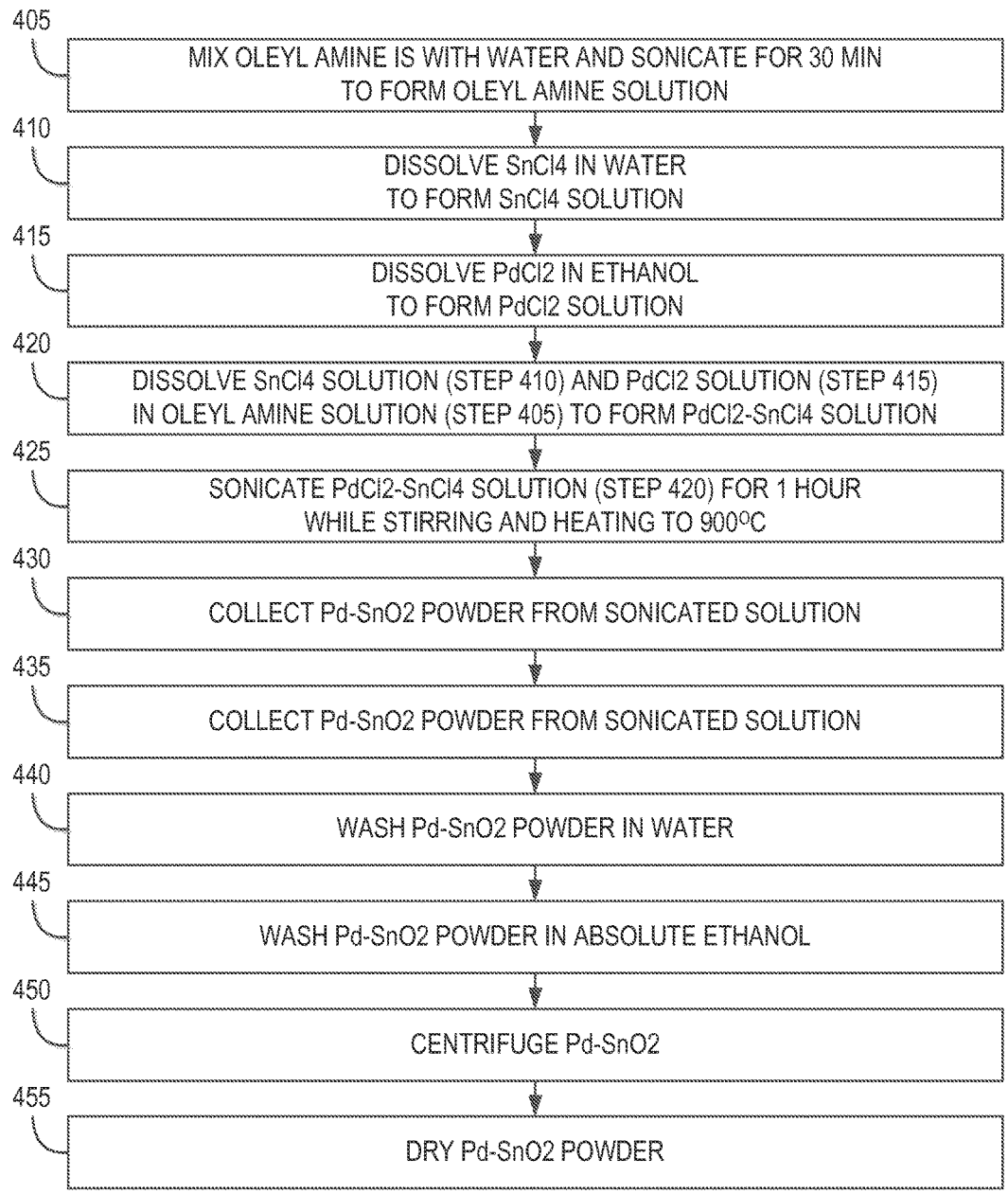
FIG. 4 is a fourth example method of sonochemical synthesis of nanostructured palladium-doped $SnO_2$ nanocomposite and sensor fabrication.

FIG. 4 is a fourth example method of sonochemical synthesis of nanostructured palladium-doped SnO$_2$ nanocomposite and sensor fabrication 400. In this fourth method 300, the precursors may include tin tetrachloride pentahydrate (SnCl$_4$*5H$_2$O) and palladium chloride. Chemical reagents for precursor dissolution and controlling hydrolysis, polycondensation, and nanostructuring may include urea (CH$_4$N$_2$O), oleyl amine (C$_{18}$H$_{35}$NH$_2$), DI water, and ethanol. Urea may be used as a reagent for pH control, which may provide a homogeneous precipitation by thermal decomposition of urea to ammonium hydroxide. Oleyl amine is a surfactant, which may be used for nanostructuring growth and control.

At 405, an appropriate amount of oleyl amine may be mixed with water and sonicated for about 30 min to form an oleyl amine solution. At 410, an appropriate amount of SnCl$_4$ may be dissolved in an aqueous solution (e.g., water) to form a SnCl$_4$ solution. At 415, an appropriate amount of PdCl$_2$ may be dissolved in ethanol to form a PdCl$_2$ solution. At 420, the SnCl$_4$ solution from 410 and the PdCl$_2$ solution from 415 may be dissolved into the oleyl amine solution from 405 to form a PdCl$_2$—SnCl$_4$ solution. At 425, the PdCl$_2$—SnCl$_4$ solution may be sonicated for 1-3 hours while stirring and heating to 90° C. to form a Pd—SnO$_2$ solution. For example, the sonication may be performed by exposing the solution to 24 KHz acoustic irradiation at 100 W (260 W/cm$^2$) for the 1-3 hour duration. At 430 and while sonicating, ammonia may be drop-wise added to the sonicating solution until the pH reaches a value of 9. The Pd—SnO$_2$ powder may be collected from the Pd—SnO$_2$ solution at 435, washed with water at 440, washed with absolute ethanol at 445, centrifuged at 450, and dried in an oven at 100° C. for 2-4 hours at 455. Following 455, the Pd—SnO$_2$ powder may be used to prepare thin sensing film or thick sensing film, as shown and described with respect to FIGS. 5A-5B.

Figure 5A:
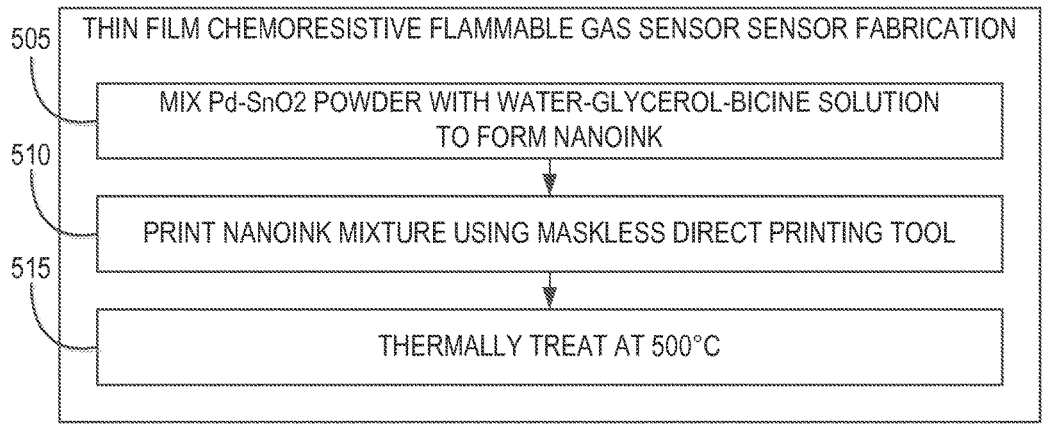
FIG. 5A is an example method of thin film Pd—$SnO_2$ chemoresistive flammable gas sensor fabrication.

FIG. 5A is an example method of thin film Pd—SnO$_2$ chemoresistive flammable gas sensor fabrication 500. The thin film sensor fabrication 500 may be performed following the drying of the Pd—SnO$_2$ powder at 165, 245, 355, or 455. At 505, the Pd—SnO$_2$ powder may be mixed with water-glycerol-bicine solution to form a nanoink. The nanoink may have associated controlled rheological properties that enable it to be compatible with maskless direct printing tool, such as the maskless direct printing tool provided by "OPTOMEC" or "Nanoink." At 510, the nanoink mixture may be printed using maskless direct printing tool. At 515, the printed nanoink may be heated and dried at about 500° C. to form a thin film Pd—SnO$_2$ chemoresistive flammable gas sensor.

Figure 5B:
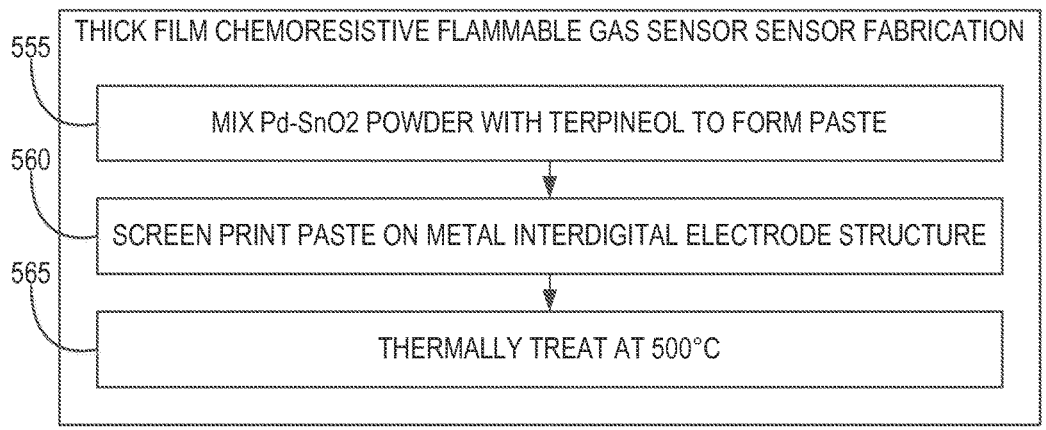
FIG. 5B is an example method of thick film Pd—$SnO_2$ chemoresistive flammable gas sensor fabrication.

FIG. 5B is an example method of thick film Pd—SnO$_2$ chemoresistive flammable gas sensor fabrication 550. The thick film sensor fabrication 550 may be performed following the drying of the Pd—SnO$_2$ powder at 160, 240, 350, or 450. At 555, Pd—SnO$_2$ powder may be mixed with terpineol to form a Pd—SnO$_2$ paste. At 560, the Pd—SnO$_2$ paste may be screen printed on a metal interdigital electrode structure. At 565, the screen printed interdigital electrode structure may be heated and dried at about 500° to form a thick film Pd—SnO$_2$ chemoresistive flammable gas sensor.

Example 1 includes a one-pot method of making a nanostructured metal oxide, the method comprising obtaining an aqueous solution, the aqueous solution comprising a tin(IV) oxide source, a palladium(II) oxide source, and a nanostructuring guiding agent, and sonicating the aqueous solution to form a solution comprising a nanostructured palladium-doped tin dioxide.

Example 2 includes the method of example 1, further comprising isolating the nanostructured palladium-doped tin dioxide.

Example 3 includes the method of any of examples 1-2, further comprising washing the nanostructured palladium-doped tin dioxide with an organic solvent.

Example 4 includes the method of any of examples 1-3, further comprising centrifuging and drying the nanostructured palladium-doped tin dioxide to form a nanostructured palladium-doped tin dioxide powder.

Example 5 includes a flammable gas sensor comprising the nanostructured metal oxide made by the method of example 1.

Example 6 includes a method of making the flammable gas sensor of any of examples 1-5, the method comprising combining the nanostructured palladium-doped tin dioxide powder with an alcohol solution to form a slurry, and depositing the slurry on a dielectric substrate.

Example 7 includes the method of any of examples 1-6, further comprising thermally treating the deposited slurry for thermal consolidation of the nanostructured palladium-doped tin dioxide powder on the dielectric substrate.

Example 8 includes the method of any of examples 1-7, wherein the thermally treating comprises heating the slurry to at least 500° C.

Example 9 includes the method of any of examples 1-7, wherein the nanostructured palladium-doped tin dioxide powder is between 0.1% and 2% by weight of Pd.

Example 10 includes the method of any of examples 1-6, wherein the alcohol solution comprises monoterpene alcohol, Example 11 includes the method of any of examples 1-6, wherein the alcohol solution comprises glycerol and bicine.

Example 12 includes the method of any of examples 1-6, wherein depositing the slurry on a dielectric substrate comprises screen-printing the slurry on the dielectric substrate, Example 13 includes the method of any of examples 1-6, wherein the dielectric substrate comprises a metallic interdigitated (IDE) structure, Example 14 includes the method of example 1, wherein the aqueous solution comprises ethanol and ammonium hydroxide, the tin oxide source comprises tin tetrachloride, the palladium source comprises palladium chloride, and the nanostructuring guiding agent comprises cetyltrimethylammonium bromide (CTAB).

Example 15 includes the method of example 1, wherein the aqueous solution comprises ethanol, the tin oxide source comprises tin (II) acetate, the palladium source comprises palladium acetate, and the nanostructuring guiding agent comprises ditnethylformamide, Example 16 includes the method of example 1, wherein the aqueous solution comprises 2-methoxyethanot, the tin oxide source comprises dihutyltindiacetate, the palladium source comprises palladium acetate, and the nanostructuring guiding agent comprises dimethylformamide.

Example 17 includes the method of example 1, wherein the aqueous solution comprises urea and ethanol, the tin oxide source comprises tin tetrachloride, the palladium source comprises palladium chloride, and the nanostructuring guiding agent comprises oleyl amine ($C_{18}H_{35}NN_2$).

Example 18 includes the method of example 1, wherein the aqueous solution comprises ammonia, citric acid, and ethanol, the tin oxide source comprises tin tetrachloride, the palladium source comprises palladium chloride, and the nanostructuring guiding agent comprises a tetraalkylammonium salt.

Example 19 includes the method of example 1, wherein the aqueous solution comprises ammonium hydroxide, ethanol, and hydrochloric acid, the tin oxide source comprises tin (II) chloride, the palladium source comprises palladium chloride, and the nanostructuring guiding agent comprises a poly(ethylene glycop-poly(propylene glycol)-poly(ethylene glycol) triblock copolymer, Example 20 includes a method of making the flammable gas sensor of any of examples 1-5, the method comprising combining the nanostructured palladium-doped tin dioxide powder with a water-glycerol-bicine solution to form a nanoink mixture, printing the nanoink mixture using a maskless direct printing tool, and thermally treating the printed nanoink mixture, The above Detailed Description is intended to be illustrative, and not restrictive, For example, the above-described examples (or one or more elements thereof) may be used in combination with each other. Other embodiments may be used, such as by one of ordinary skill in the art upon reviewing the above description. In addition, various features or elements may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." The terms "including" and "comprising" are open-ended, that is, a. system or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

All publications, including non-patent literature (e.g., scientific journal articles), patent application publications, and patents mentioned in this specification are incorporated by reference as if each were specifically and individually indicated to be incorporated by reference.

The Abstract is provided to allow the reader to ascertain the nature of the technical disclosure quickly. It is submitted with the understanding that it will not be used to interpret or limit the scope or meaning of the claims.

What is claimed is:

1. A one-pot method of making a nanostructured metal oxide, the method comprising:
   obtaining an aqueous solution, the aqueous solution comprising a tin (IV) oxide source, a palladium (II) source, and a nanostructuring guiding agent; and
   sonicating the aqueous solution to form a solution comprising a nanostructured palladium-doped tin dioxide.

2. The method of claim 1, further comprising isolating the nanostructured palladium-doped tin dioxide.

3. The method of claim 2, further comprising washing the nanostructured palladium-doped tin dioxide with an organic solvent.

4. The method of claim 3, further comprising centrifuging and drying the nanostructured palladium-doped tin dioxide to form a nanostructured palladium-doped tin dioxide powder.

5. The method of claim 1, wherein:
   the aqueous solution comprises ethanol and ammonium hydroxide;
   the tin oxide source comprises tin tetrachloride;
   the palladium source comprises palladium chloride; and
   the nanostructuring guiding agent comprises a tetraalkylammonium salt.

6. The method of claim 1, wherein:
   the aqueous solution comprises ethanol;
   the tin oxide source comprises tin (IV) acetate;
   the palladium source comprises palladium acetate; and
   the nanostructuring guiding agent comprises dimethylformamide.

7. The method of claim 1, wherein:
   the aqueous solution comprises 2-methoxyethanol;
   the tin oxide source comprises dibutyltindiacetate;
   the palladium source comprises palladium acetate; and
   the nanostructuring guiding agent comprises dimethylformamide.

8. The method of claim I, wherein:
   the aqueous solution comprises urea and ethanol;
   the tin oxide source comprises tin tetrachloride;
   the palladium source comprises palladium chloride; and
   the nanostructuring guiding agent comprises oleyl amine ($C_{18}H_{35}NH_2$).

9. The method of claim 1, wherein:
   the aqueous solution comprises ammonia, citric acid, and ethanol;
   the tin oxide source comprises tin tetrachloride;
   the palladium source comprises palladium chloride; and
   the nanostructuring guiding agent comprises a tetraalkylamtnonium salt.

10. The method of claim 1, wherein the aqueous solution comprises ammonium hydroxide, ethanol, and hydrochloric acid;
    the tin oxide source comprises tin (IV) chloride;
    the palladium source comprises palladium chloride; and
    the nanostructuring guiding agent comprises a poly(ethylene glycol)-poly(propylene glycol)-poly(ethylene glycol) triblock copolymer.

11. A flammable gas sensor comprising the nanostructured meta oxide made by the method of claim 1.

12. A method of making the flammable gas sensor of claim 11, the method comprising:
    combining the nanostructured palladium-doped tin dioxide powder with an alcohol solution to form a slurry; and
    depositing the slurry on a dielectric substrate.

13. The method of claim 12, further comprising thermally treating the deposited slurry for thermal consolidation of the nanostructured palladium-doped tin dioxide powder on the dielectric substrate.

14. The method of claim 13, wherein the thermally treating comprises heating the slurry to at least 500° C.

15. The method of claim 12, wherein the nanostructured palladium-doped tin dioxide powder is between 0.1% and 2% by weight of Pd.

16. The method of claim 12, wherein the alcohol solution comprises monoterpene alcohol.

17. The method of claim 12, wherein the alcohol solution comprises glycerol and bicine.

18. The method of claim 12, wherein depositing the slurry on the dielectric substrate comprises screen-printing the slurry on the dielectric substrate.

19. The method of claim 12, wherein the dielectric substrate comprises a metallic interdigitated (IDE) structure.

20. A method of making the flammable gas sensor of claim 11, the method comprising:
- combining the nanostructured palladium-doped tin dioxide powder with a water-glycerol-bicine solution to form a nanoink mixture;
- printing the nanoink mixture using a maskless direct printing tool; and
- thermally treating the printed nanoink mixture.

* * * * *